United States Patent [19]

Fleer

[11] Patent Number: 4,669,982
[45] Date of Patent: Jun. 2, 1987

[54] DENTAL HANDPIECE ARRANGEMENT WITH AN ILLUMINATION DEVICE

[75] Inventor: Ernst-Otto Fleer, Bensheim, Fed. Rep. of Germany

[73] Assignee: Siemens Aktiengesellschaft, Berlin and Munich, Fed. Rep. of Germany

[21] Appl. No.: 809,036

[22] Filed: Dec. 16, 1985

[30] Foreign Application Priority Data

Dec. 21, 1984 [DE] Fed. Rep. of Germany ....... 3447743

[51] Int. Cl.$^4$ ............................................... A61C 3/00
[52] U.S. Cl. ...................................... 433/29; 433/126
[58] Field of Search .................................. 433/29, 126

[56] References Cited

U.S. PATENT DOCUMENTS

4,514,169  4/1985  Strohmaier ............................ 433/29
4,568,284  2/1986  Stankiewicz ........................... 437/29

Primary Examiner—Robert Peshock
Attorney, Agent, or Firm—Hill, Van Santen, Steadman & Simpson

[57] ABSTRACT

A dental handpiece arrangement having a drive motor mounted in a motor cartridge which is connectible to a supply hose supplying various fluids and electrical power, a coupling member being mounted on the cartridge at one end and a sleeve member being telescopically received on the cartridge and either being an extension of a dental grip piece or an adapter for receiving conventional grip pieces characterized by an illumination arrangement which can either be a light source in the coupling member connected by optical waveguides extending through the sleeve member and the grip piece or can be an electrical connector connected to an electrical lead extending through the sleeve member to a light source either in the sleeve member or the grip piece so that both existing conventional grip pieces with or without the sleeve member can be utilized with the cartridge and coupling member regardless of the type of illumination arrangement being provided therein.

18 Claims, 18 Drawing Figures

DENTAL HANDPIECE ARRANGEMENT WITH AN ILLUMINATION DEVICE

BACKGROUND OF THE INVENTION

The present invention is directed to a dental handpiece arrangement having a drive motor with a drive shaft and a grip piece containing a grip sleeve with a head housing having a chuck arrangement to hold a tool which is rotated by a drive train that is connected to the drive shaft of the drive motor and an illumination arrangement to provide light in the work area of the tool.

It has been known for a long time in dental technology to mount with a removable connection a handpiece part which essentially contains a head housing with a gripping sleeve connected and is referred to in the technical field as a "hand and angle piece", on a drive part containing a drive motor. The connection is designed so that in its emplaced condition, the hand and angle piece can be rotated relative to the drive part while retaining the drive shaft connection. The coupling and uncoupling occurs by means of a rapid coupling via a guide sleeve which surrounds the drive shaft of the drive part as disclosed in U.S. Pat. No. 3,604,960. The connecting parts of the rigid coupling have dimensions which are according to ISO standards.

The construction of such a handpiece arrangement has been retained even with the introduction of what is referred to as an incorporated spray arrangement, i.e., the guidance of a cooling agent such as air and water within the drive parts and within the hand and angle piece. The guidance of the agent within the drive part is between the stator and motor housing and the agent is delivered at the guide sleeve or pin for transfer to the grip piece through a fluid coupling arrangement which includes radially extending ports in either one of the guide pins or socket of the grip piece and the other of the guide pins and socket having annular channels with O-ring seals for receiving the discharge from the ports. Such an arrangement is disclosed in U.S. Pat. No. 4,007,529.

A handpiece arrangement that is suitable for conventional hand and angle pieces is also known and incorporates the light guidance. For example, a light is guided within the handpiece part as disclosed in U.S. Pat. No. 4,518,355 which claims priority from German Patent Application No. 32 15 219. In one of these known embodiments, the light generator, which is an incandescent lamp, is situated at the acceptance part rotatably held on the drive part. Here, the hand and angle piece contains a light guide which extends from the head housing up to the motor side end and this light guide is positioned opposite the lamp in a corresponding fashion in the coupled condition. Mechanical dog elements are provided between the hand and angle piece and the acceptance parts which bring the light generator and the corresponding end of the light guide into coincidence when the two parts are coupled together so that the two parts will rotate together. Accordingly, contacts comprising slip rings are provided between the acceptance parts and the drive parts to provide power to the incandescent bulb.

In other known embodiments, the light generator is situated in an acceptance part which is rotatably situated at the back end of the drive part.

A handpiece arrangement is also known from European Patent No. 00 34 237 wherein the light generator is situated outside of the handpiece arrangement, for example, in a supply unit. Light from this unit is then supplied to the handpiece by optical light guides in a supply hose and also is transmitted between the various parts of the handpiece by light guides. Given this arrangement, the hand and angle piece is torsionally connected to the drive part after it has been coupled thereto and rotatability here occurs between the drive part and the connection part of the supply line.

In addition to these conventional handpiece arrangements, a handpiece arrangement wherein the gripping sleeve normally remains on the drive part and only relative short treatment heads containing the head housing are coupled to the drive part in an easily releasable fashion have also become common in recent years. The gripping sleeve will have a sleeve extending over the drive part which contains the agent guidance, and the gripping sleeve itself is only removed from the drive part for sterilization purposes. The gripping sleeve and the treatment head are freely rotatable relative to the drive part but the sleeve extending over the motor is not and it is capable of being withdrawn from the drive part together with the gripping sleeve as disclosed in U.S. Pat. No. 4,251,212. This type of handpiece arrangement has not been disclosed with any illumination device, however, there is a desire to be able to offer such a motor-driven handpiece arrangement which incorporates an illumination arrangement with light guidance.

Various different types of disclosed structures for the arrangement of light illumination in a gripping sleeve is due to the fact that the customer, dependent on the equipment of his device, can necessarily only employ handpieces or, respectively, grip sleeve embodiments provided for one or another construction of the drives, i.e., conventional "hand and angle pieces" with or without lights can only be coupled to conventional drive parts. Handpieces, whose rotatability is provided at the guide sleeve and handpieces whose rotatability is provided in a back part of the drive part can hereby only be respectively coupled to drive parts which are designed to fit these particular types of structures.

SUMMARY OF THE INVENTION

The present invention is directed to creating a handpiece arrangement where one and the same drive motors can be provided both for the use of conventional hand and angle pieces as well as for the use of hand parts extending over the motor which are already known and under given conditions even such other handpiece parts whereby both light guiding handpieces as well as handpieces without light could be coupled to the drive motor. In addition, the illumination arrangement of the handpiece can include conducting light through the handpiece as well as conducting power to a light generator or bulb positioned somewhere in the handpiece.

These objects are accomplished by an improvement in the construction of a dental handpiece arrangement having a drive motor with a drive shaft, a grip piece having a head housing with chuck means to hold and rotate a tool, a drive train extending in the grip piece to connect the drive shaft to the chuck means and illumination means for providing light in the work area of the tool. The improvements comprise a drive motor being received in a cylindrical motor cartridge with the drive shaft extending out of a cylindrical coupling element at one end of the cartridge which coupling element has a smaller diameter than the diameter of the cartridge, said cartridge at the other end having means for releasably connecting with a pin member of a supply hose containing electrical leads and water and air lines, said motor cartridge having at least two cylindrical bearing surfaces axially spaced therealong for coacting with internal bearing surfaces of a cylindrical sleeve which is telescopically received on the cartridge and may be part of an adapter or part of a grip piece, said cylindrical sleeve having a coupling element coacting with said cylindrical coupling element to form latch means for securing the sleeve on the motor cartridge, a sleeve-shaped coupling member, mounting means for mounting the sleeve member at the other end of the cartridge and connected to said pin member for rotation relative thereto, said sleeve-shaped coupling member having means for coupling air and water discharging from the pin member into fluid channels extending to sockets for receiving fluid conduits of the sleeve member to form connections therewith so that fluid is coupled through the coupling member to the sleeve member and said coupling member having a recess facing the sleeve member receiving an electrical socket for an electrical element of the illumination means selected from a group consisting of an electrical connection and an electrical lamp, said socket being connected to the means for receiving electrical energy from said slip rings so that the coupling member may be constructed to provide a light source for a light-conducting element in the sleeve member extending through a grip piece for discharge adjacent the tool or may receive an electrical plug connection of an electrical lead to conduct electrical power along the grip sleeve to a light source positioned closer to the head housing.

Since the motor cartridge normally contains only motor associated parts and is thus neutral with respect to the light conduction, it can accept either an electrical motor or an air motor. The feed of electrical energy required for generating light occurs from the pin member of the supply hose into the sleeve-like coupling member, which is mounted for rotation with respect thereto. This coupling member will contain connecting elements for alternate connection of either a lamp or part of a plug-type connection for electrical lines and thus it is possible to alternately attach the handpiece parts having an integrated light guide system or a handpiece part having an integrated lead extending to a lamp without undertaking substantial structural modifications of the coupling member. In addition, conventional hand and angle pieces as well as those having a sleeve extending over the motor can also be very easily connected, namely, either again with an integrated transmission element conducting the light from the coupling member or on the other hand with a light generator integrated into the hand and angle piece with the electrical leads extending along the sleeve of the handpiece to the coupling member. In the case of conventional hand and angle pieces, this can be achieved by means of a relatively simple adapter which contains a guide sleeve having standardized dimensions such as set forth by ISO on the end of the motor housing facing the handpiece side. When as proposed in accordance with further advantageous developments of the invention, the adapter itself is fashioned such that at its end face that it alternately accepts an incandescent lamp the other part of the plug-type coupling or slip ring contacts. Then the hand and angle piece which has either a light generator or elements for conducting light can be attached to this adapter.

Other advantages and developments will be readily apparent from the following description, drawings and claims.

DESCRIPTION OF THE PREFERRED EMBODIMENTS

Figures 1, 2, 3, 4, 5, 6:
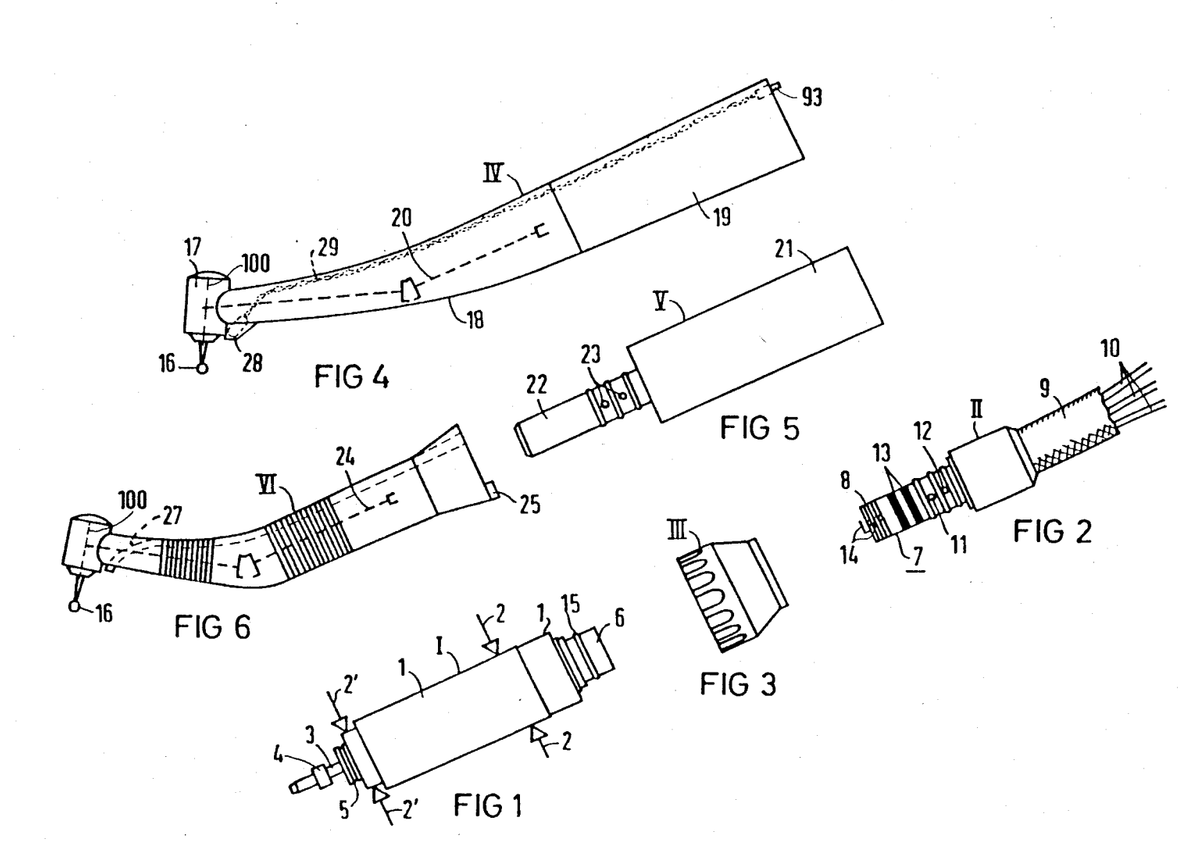
FIG. 1 is a side view of a motor cartridge of the present invention.
FIG. 2 is a side view of a connecting part for a supply hose in accordance with the present invention.
FIG. 3 is a side view of a coupling member in accordance with the present invention.
FIG. 4 is a side view of one type of handpiece having a gripping sleeve with a sleeve portion for receiving the motor cartridge in accordance with the present invention.
FIG. 5 is a side view of an adapter having a gripping sleeve portion for receiving the motor cartridge in accordance with the present invention.
FIG. 6 is a side view of an angled handpiece for use with the adapter of FIG. 5 in accordance with the present invention.

The principles of the present invention are particularly useful in a dental handpiece arrangement having a motor cartridge I of FIG. 1. The motor cartridge I comprises an essentially cylindrical element 1, which has two slide bearing surfaces indicated by the arrows 2 and 2' which are axially spaced along the axis of the cartridge and as illustrated, one of the slide bearing surfaces 2' is of a smaller diameter than the other bearing surface 2.

The motor cartridge I basically accepts only the motor parts such as the rotor with a shaft 3, rotor shaft bearings, stator, brushes and brush mounts or holders. Instead of an electric motor, the cartridge I can contain an air motor. An end of the motor shaft 3 extends from one end of the cartridge I and is provided with a dog 4 which couples the shaft to corresponding drive sections of the handpiece part in a known fashion when the handpiece part is plugged onto the motor cartridge as discussed hereinafter. As illustrated, an annular coupling element 5 having a groove is disposed on the one end of the cartridge and the shaft end 3 extends therethrough. An annular groove of the element 5 coacts with a catch 90 (FIG. 9) of an adapter V or a catch of a handpiece IV to form a latch means by which a handpiece part, which is telescopically received on the outer surface of the cartridge I, is axially retained on the cartridge but can rotate relative to the cartridge I.

The cartridge I on the other end has mounting means in the form of a cylindrical heel or sleeve 6 whose outside diameter is significantly smaller in comparison to that of the cylindrical portion or part 1. The sleeve or heel 6 has an axial opening with internal threads receiving a tappet or pin 7 of a connector part II. The tappet or pin 7 is provided with threads 8 which coact with the threads of the heel 6 to form a non-rotatable rigid but detachable connection between the motor cartridge I and the connector part II.

The connector part II is secured on a supply hose 9 which has a plurality of leads or feed lines 10. Two of the feed lines 10 supply air and water and have radial discharge openings or ports 11 and 12 on the circumference of the pin 7, which openings 11 and 12 are sealed from one another by O-rings in a conventional manner. Electrical power is supplied on electrical leads and are connected to a pair of axially spaced slide rings 13 on the circumference of the pin and also to contacts 14 disposed at an end of the pin 7. The contacts 14 are composed of a contact socket which is in the center of the pin 7 and of a contact spring situated concentrically thereto. The slip rings 13 serve for supplying electrical energy to an illumination means which will be described hereinafter. The contact pair 14 serve for supplying the necessary electrical energy to the motor of the cartridge I.

Figure 7:
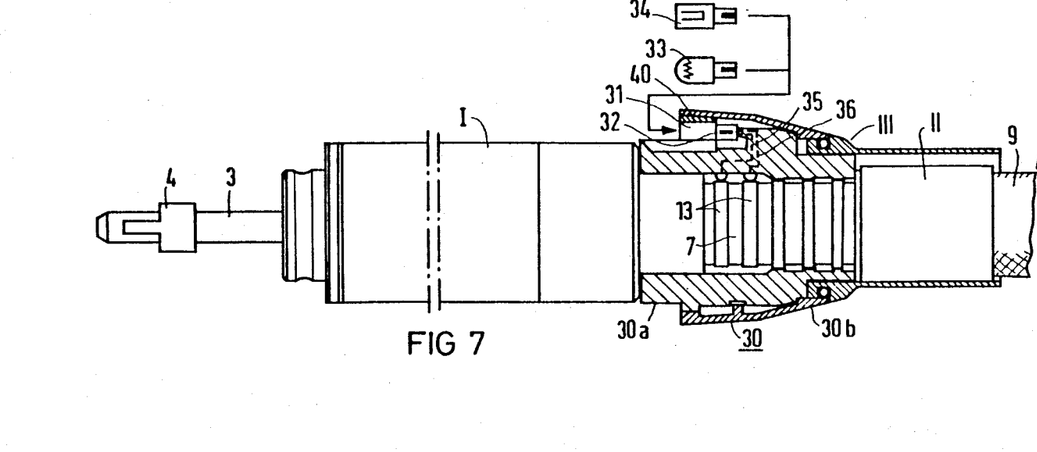
FIG. 7 is a partial cross-sectional view of an assembly of the motor cartridge of FIG. 1, the coupling part of FIG. 2 and the coupling member of FIG. 3.

A feature of the assembly is a coupling member or ring III of FIG. 3 which is telescopically received on the heel 6 prior to forming the connection between the pin 7 and the socket of the heel 6. To allow rotation of the coupling member 111 on the heel 6, it is provided with means such as an annular groove (not illustrated) which coacts with an annular groove on the heel 6 and receives an O-ring 15. Thus, with the coupling member III assembled on the heel 6, an arrangement or assembly such as illustrated in FIG. 7 will be obtained.

After assembly of the coupling member III onto the motor cartridge I and subsequently screwing of the connecting pin 7 of the connecting part II to the motor cartridge I, either a handpiece IV of FIG. 4 or an adapter V of FIG. 5 can be alternately attached and latched or secured against axial slipping off of the cartridge I by the above-mentioned latching means. It should be noted that the latching means allows either the handpiece IV or the adapter V to be rotated on the cartridge I. When the adapter V of FIG. 5 is slipped onto the cartridge, then a handpiece VI of FIG. 6 is telescopically mounted on the adapter.

When, as in the presently illustrated embodiment, the connection pin 7 of the supply hose 9 is torsionally connected to the motor cartridge I and the coupling member III is rotatably situated relative to these two parts, then an embodiment is also alternately conceivable wherein the coupling member III is a component part of the motor cartridge I. For example, it is torsionally secured thereto and the connection pin 7 is held by the motor cartridge in a rotational fashion secured against axial disconnection, for example, in the projection 6. The measures for generating light and/or respectively for guiding light set forth in greater detail hereinbelow accordingly apply to this alternate solution as well.

The handpiece IV of FIG. 4 is the type of handpiece part wherein the head housing 17 has chuck means 100 which receives a tool 16 and rotates the tool on the axis thereof. The housing 17 forms a unit with a gripping sleeve 18 which extends up to the motor side and then has an additional tubular sleeve 19 for extending over the motor cartridge I. It should be noted that the sleeve 19 has internal bearing surfaces which are received on the two axially spaced bearing surfaces 2 and 2' of the cartridge I. In the plugged-in condition, the motor or drive shaft 3 is coupled by the dog 4 to a drive train 20 which is composed of at least two drive shaft sections that extend through the gripping sleeve 18 to the chuck means 100 so that the rotation of the drive motor shaft 3 will be transferred to rotate the tool 16.

The adapter V (see FIG. 5) contains a sleeve-shaped section 21 and a pilot or guide sleeve 22 extending from one end of the sleeve-shaped section 21. As illustrated, the guide sleeve has a plurality of radial discharge openings 23 axially spaced therealong and separated by O-rings. When the adapter V is secured on the motor cartridge I, the sleeve 22, which has standard dimensions according to ISO, in addition to surrounding the drive shaft 3 and the dog 4, will receive a mounting socket of a grip piece VI. The mounting socket of the piece VI has corresponding channels which match the radial openings 23 so that fluid such as air and water being transferred through the ports 23 is received and conveyed through the grip piece VI in a conventional manner for discharge adjacent the tool 16. In addition, when the grip piece VI is assembled on the adapter V, a drive train 24 of drive shaft sections will be coupled to the dog 4 for transferring rotation of the shaft 3 to drive or rotate the chuck means 100 holding the tool 16. As illustrated, the end of the handpiece VI has a nose 25 which actuates a switch in a manner discussed hereinafter when the handpiece is assembled on the adapter V.

The two handpiece parts IV and VI are provided with illumination means for projecting light in the proximity of the head housing 17 to illuminate the area in which the tool 16 is acting on. The illumination means can either be a light guide extending to the head housing or can comprise a miniature incandescent lamp which is positioned at the suitable location which is expediently in the proximity of the head housing such as 17. When the incandescent lamp is provided, feed cable is laid to proceed from the lamp to the other end of the handpiece part.

In the presently illustrated embodiments, it is assumed that the conventional and angle piece shown in FIG. 6 is equipped with a light guide 27 which is illustrated in a simplified form in the Figure. The light guide 27 extends from a point adjacent the tool 16 to a point adjacent the mounting socket and the end of the handpiece. In the embodiment of the handpiece part IV illustrated in FIG. 4, an incandenscent lamp 28 is situated in the region of the head housing 17 and is supplied with the necessary electrical current by a feed cable or electrical lines 29 which extends back through the sleeve portions 18 and 19 to a connecting element 93. The laying of the light guide 27 or respectively the feed cable 29 within the handpiece parts IV and VI does not present a problem per se. Therefore, it has not been discussed in greater detail.

Since the guidance of the cooling agent such as air and water are not of significance to the present invention, the course of the cooling agent shall not be shown in detail in the following Figures. Thus, the conveying of the air and water either separately or combined through the adapter V and through the handpiece part VI or through the handpiece part IV has not been illustrated or described in detail. However, the measures for generating light for the illumination means and for conveying the light within the handpiece arrangement are set forth hereinbelow and the various possibilities which occur for the basis of the handpiece arrangement of the invention shall be set forth with references to FIGS. 7 and 9.

In accordance with a preferred embodiment, the drive cartridge I, as already mentioned, is torsionally connected to the connecting pin 7 of the connecting part II and the coupling member III is rotatably received on the heel 6 and surrounds the pin 7 of the connecting part II.

The coupling member III is essentially composed of a combination sleeve 30 having an inside sleeve 30a and an outside sleeve 30b. The inside and outside sleeves have a recess 31 into which a socket 32 is placed. The socket 32 can receive either a miniature incandescent lamp 33 or a plug socket 34 which are elements of the illumination means. The socket 32 comprises electrical contacts insulated from one another which will mate with the correspondingly fashioned contacts of either the lamp 33 or the plug socket 34 and are connected to leads 35 and 36 whose ends are resiliently pressed against the slip rings 13 of the pin 7. The recess 31 for the alternative acceptance of an incandescent lamp or the plug socket 34 is situated so that in the assembled condition, the incandescent lamp 33 or, respectively, the openings for the plug socket 34 project radially beyond the circumferential surface of the motor housing of the cartridge I as shown in FIG. 8 so that the handpiece parts IV or V can be plugged or slipped onto the motor cartridge and the elements of the lamp or respectively of the plug socket can be connected to either convey the light through an optical waveguide of the handpiece part or electricity through electrical lines in the handpiece part.

Figure 8:
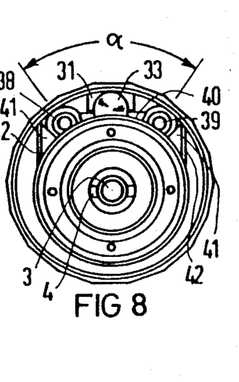
FIG. 8 is an end view of the assembly of FIG. 7 taken from the left side.

As may be seen from FIG. 8, which is the assembly of FIG. 7 with the lamp 33 inserted into the socket 32, the coupling member has connecting sockets 38 and 39 for water and air which are situated on opposite sides with the lamp 33. The connecting sockets for air and water and the lamp sockets are all advantageously combined in an insertable mounting part 40 over a relatively tight and limited angular range α of approximately 60° to 70° of the circumference. The sockets 38 and 39 are constructed so that correspondingly fashioned cooperating elements of the handpiece parts pluggable onto the motor carriage I can be coupled to them. The mounting part 40, which is situated in the outer sleeve 30b has a dog part 41 having mutually parallel extending surfaces 42 which come into engagement with the corresponding cooperating surfaces such as 58 of a cooperating element 59 (see FIG. 12) of the handpiece part when the handpiece part is telescopically received on the motor cartridge I. Thus, the coaction between the dog parts 41 and 59 insure that the handpiece part and the coupling member III will rotate together.

The adapter V (see FIG. 9) can be telescopically placed on the motor cartridge I and is composed of a thin outer sleeve 43 forming an outer cladding or surface and an inner part or sleeve 44 whose inside contour corresponds to the outside contour of the motor cartridge I and in particular comprises guide or bearing surfaces necessary for rotation on the corresponding bearing locations 2 and 2'. On an outer periphery, the insert part 44 contains recesses 45, which, together with the outside sleeve 43, form an annular space in which on the one hand lines or tubes (not shown) for the passage of air and water can extend and on the other hand a switch rod 46 is mounted. When a grip piece VI is mounted on the adapter V a dog or projection 25 shifts the switch rod 46 to activate a switch in the coupling element.

Figure 9:
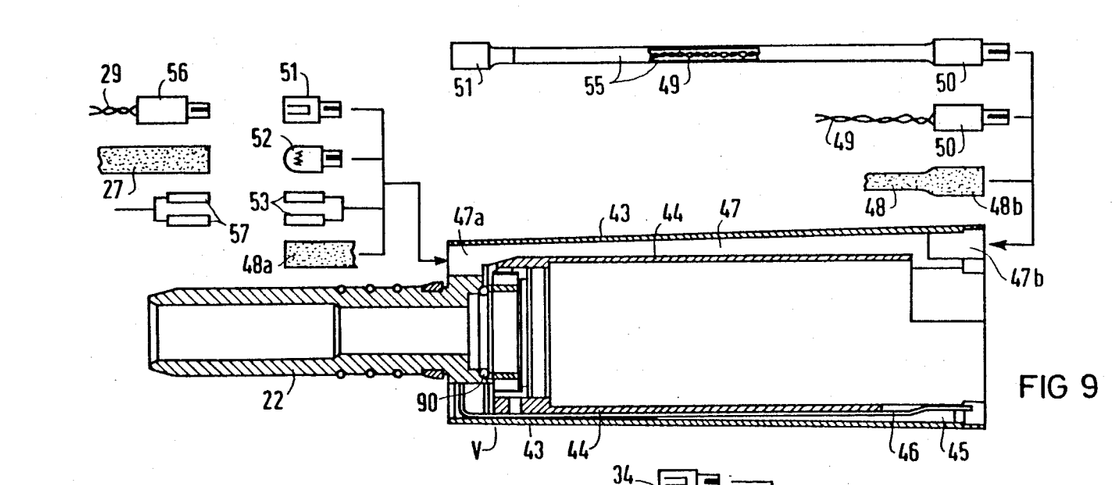
FIG. 9 is a longitudinal cross-sectional view of the adapter of FIG. 5 illustrating the various possible combinations of transmission parts and elements that can be carried therein for conducting light or electricity.

The parts placed in the annular space are situated such that the space lying therebetween can be used for the passage of cooling air for cooling the motor. The cooling air first flows through the coupling member III so that the lamp 33 will be cooled by the air prior to it entering into the annular space 45. After flowing along the space 45, it will flow to enter openings in the cartridge I to flow through the cartridge for cooling purposes.

In addition to the above-mentioned passage or channel 45, an additional guide channel 47 is provided in the adapter V. This guide channel 47 serves to mount transmission elements which can be either a light guide or optical waveguide 48 or an electrical line 49, which electrical line 49 is provided with plug-in or wiper contacts 50, 51 or 53. The channel 47 has ends 47a and 47b which are constructed so that the first end 47b can receive one end 48b of a light guide 48 or a plug or connector 50 which will mate with the plug socket 34 held in the socket 32 of the coupling member III. The opposite or second end 47a of the channel 47 will either have the opposite end 48a of the light guide or can have a socket 51 which is similar to the plug socket 34 and can either receive an incandescent lamp 52 or a plug 56 of an electrical line 29. In addition, instead of receiving either the socket 51 or the light waveguide end 48a, the second end 47a can have two concentric slip ring contacts 53.

It is especially advantageous when the light waveguide 48 or respectively, the electrical line 49 together with the connections 50 and 51 or 50 and 52 or 50 and 53 are provided dependent upon their particular use and are situated in a rod shape or, respectively, tube shaped insert part such as 55. This insert part 55 can be either rigid or flexible and can be inserted axially into the channel 47. It can also be radially inserted into the guide channel 47 before the sleeve 43 has been assembled on member 44.

A forwarding of the light or of the voltage in the hand and angle piece VI, which piece is plugged onto the adapter V occurs in an analogous fashion depending on whether the adapter is equipped with a lamp 52, light guide 48, a plug socket 51 or the wiper contacts 53. For example, if the adapter has either a light waveguide 48 or a lamp 52, then the handpiece part VI will have a light waveguide 27 such as illustrated in FIG. 6. However, if there is a plug socket 51, then the handpiece will have a plug 56 connected to an electrical line 29 which can extend to an incandescent bulb similar to the bulb 28 in the handpiece part IV of FIG. 4. In addition, as explained hereinbelow, if slip rings such as 53 are provided, then the handpiece part may have coacting slip rings or contacts 57 to engage these.

Figure 10:
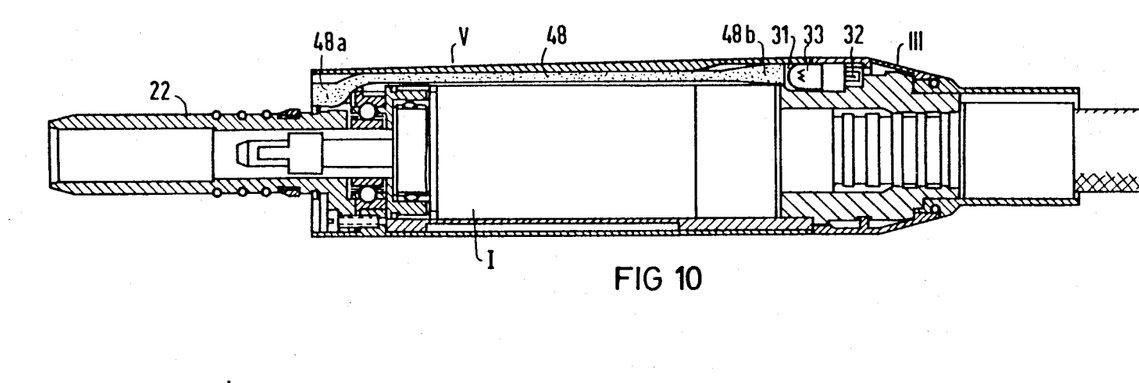
FIG. 10 is a longitudinal cross-sectional view of the assembly of FIG. 7 with the adapter of FIG. 5 assembled thereon.

An exemplary embodiment of the adapter V is illustrated in FIG. 10. As illustrated, an incandescent lamp 33 is received in the socket 32 of the coupling member III. A light waveguide 48 is positioned in the adapter to extend from the end 48b which is immediately adjacent the lamp 33 and terminates in the end 48a adjacent the guide sleeve 22. Thus, when an angle piece of FIG. 6 is plugged or received on the sleeve 22, the light guide of that angle piece will be matched to the end 48 to conduct light to be projected onto the work area of the tool or drill 16. In this arrangement, dog elements are provided, for example, in the form of a catch nose such as 25 in FIG. 6 to form a torsion or non-rotating connection between the hand and angle piece VI and the adapter V so that the hand and angle piece VI and the adapter V both rotate together.

Figure 11:
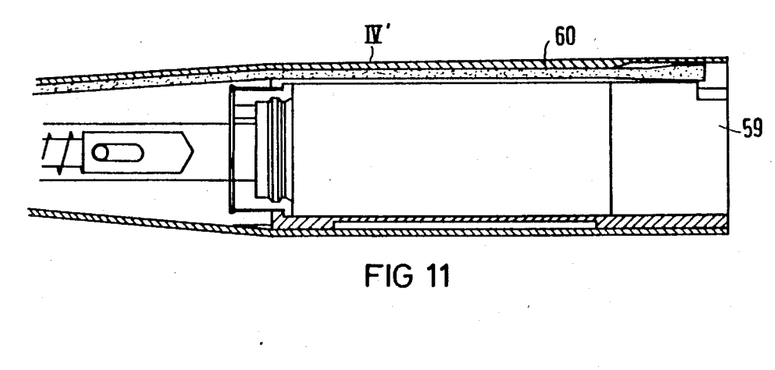
FIG. 11 is a partial longitudinal cross-sectional view taken on lines XI—XI of FIG. 12 of the handpiece part of FIG. 4.

When the adapter V is withdrawn from the motor cartridge I, then a handpiece part such as IV' which is a modification of the handpiece part of FIG. 4 can be alternately placed thereon. This handpiece part IV' is illustrated in FIG. 11 and is provided with a light guide 60 which extends from adjacent the head housing of the handpiece to the end which abuts against the coupling member III. Instead of the handpiece part IV' which has the light guide 60, the handpiece part IV having a lamp 28 can be utilized. In this arrangement, the plug 93 similar to the plugs 50 and 56 is provided and will be received into the plug socket 34 which is in the lamp socket 32 of the coupling member III instead of the lamp 33. As a consequence of the design of the lamp, particularly the lamp contacts, it is possible to fashion the lamp socket 32 such that the plugs 50 or 93 can be directly plugged into it so that the plug socket 34 can be eliminated as an adapter element.

Figure 12:
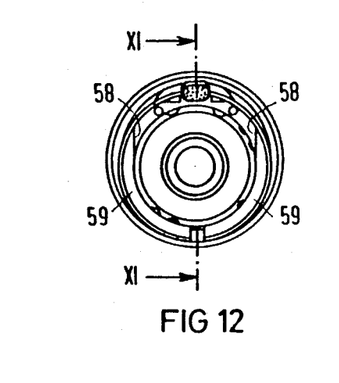
FIG. 12 is an end view piece of the handpiece part of FIG. 11 taken from the right end of FIG. 11.

As illustrated in FIG. 12, the sleeve portion of the handpiece part IV or the handpiece part IV' has an element 59 with surfaces 58 which cooperate with the surfaces 42 of the dog element 41 of the coupling element III. Thus, the handpiece part IV or IV' and the coupling element III will rotate together.

Figure 13:
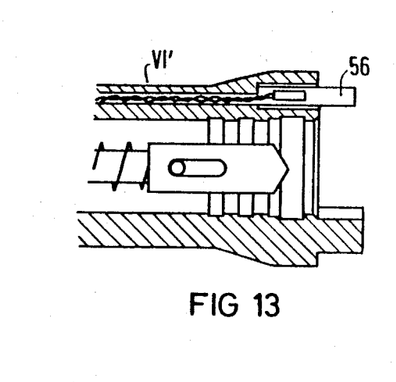
FIG. 13 is a partial longitudinal cross-sectional view of a modification of a handpiece part of FIG. 6.
Figure 14:
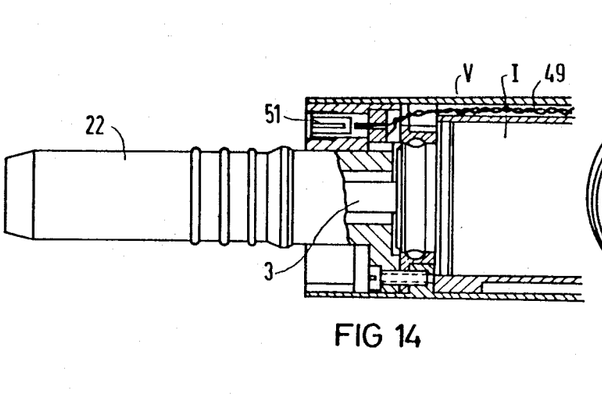
FIG. 14 is a partial longitudinal cross-sectional view with portions in elevation of a modification of the adapter of the assembly of FIG. 7 to coact with the handpiece part of FIG. 13.
Figure 15:
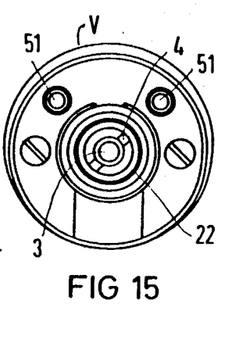
FIG. 15 is an end view taken from the left end of the assembly of FIG. 14.

In the previous discussion of the adapter V, it was mentioned that it could have electrical leads instead of the light waveguide 48. As best illustrated in FIGS. 13, 14 and 15, a handpiece VI' is provided with two plug-type connectors 56 which are received in sockets or plug connectors 51 of the adapter V. The sockets or plug connections 51 are connected by electrical lines 49 as mentioned hereinbefore. It should be noted that in this arrangement the connecting parts 51 are circumferentially spaced as best illustrated in FIG. 15.

Figure 16:
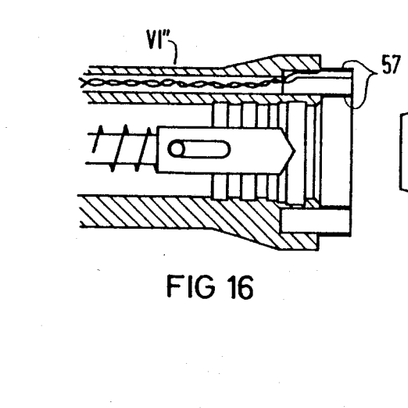
FIG. 16 is a partial longitudinal cross-sectional view of another modification of the handpiece part of FIG. 6.
Figure 17:
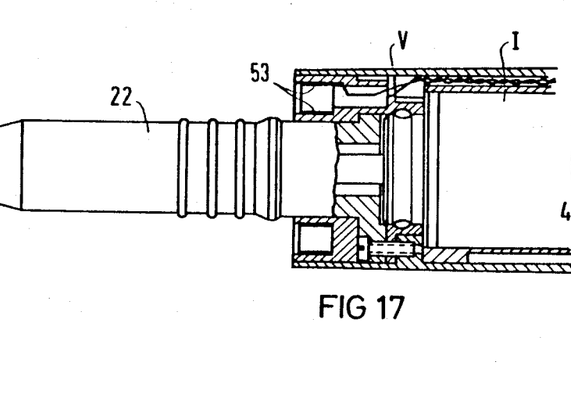
FIG. 17 is a partial longitudinal cross-sectional view with portions in elevation of another modification of the adapter on the assembly of FIG. 7 for coaction with the handpiece part of FIG. 16.
Figure 18:
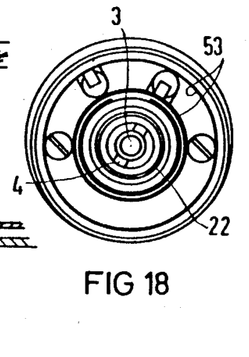
FIG. 18 is an end view taken from the left hand end of the assembly of FIG. 17.

Another modification of the adapter V is illustrated in FIGS. 16, 17 and 18. In this modification, a pair of slip rings 53 are mounted in an annular space at the end of the adapter 5 and are concentric to the guide sleeve 22. A handpiece VI'' (FIG. 16) has two cooperating contacts 57 which engage the slip rings 53. As illustrated in FIG. 16, the contacts 57 are concentric slip rings; however, instead of two pairs of concentric slip ring contacts 57 and 53 as illustrated, one of these could be replaced by a slip ring provided on the guide sleeve 22 which is engaged by a corresponding contact in the mounting socket receiving the guide sleeve 22.

Instead of the slip ring contacts 53 shown in the exemplary embodiment, two contact tongues lying radially against the contact rings 57 in the coupled condition can be utilized. In this arrangement, these two contacts could be provided in an insulated part which is inserted into one of the plug sockets 51 positioned such as illustrated in FIG. 14. In addition, it could be provided or inserted into the recess of the second end 47a of the guide channel 47. An even more universal connection possibility is established such as by contacts 53 while retaining the structural design.

Although various minor modifications may be suggested by those versed in the art, it should be understood that I wish to embody within the scope of the patent granted hereon, all such modifications as reasonably and properly come within the scope of my contribution to the art.

I claim:

1. In a dental handpiece arrangement having a drive motor with a drive shaft, a grip piece having a head housing with chuck means to hold and rotate a tool, a drive train extending in the grip piece to connect the drive shaft to the chuck means and illumination means for providing light in the work area of the tool, the improvements comprising said drive motor being received in a cylindrical motor cartridge with the drive shaft extending out of cylindrical coupling element at one end of the cartridge, which coupling element has a smaller diameter than the diameter of the cartridge, said cartridge at the other end having connection means for releasably connecting with a pin member of a supply hose containing electrical leads and water and air lines, said motor cartridge having at least two cylindrical bearing sufaces axially spaced therealong for coacting with internal bearing surfaces of a cylindrical sleeve member which is telescopically received on the cartridge and is connected to a grip piece, said cylindrical sleeve member having a coupling element coacting with said cylindrical coupling element to form latch means for securing the sleeve member on the motor cartridge, a sleeve-shaped coupling member, mounting means for mounting the coupling member at the other end of the cartridge and concentric to said pin member for rotation relative to the pin member, said sleeve-shaped coupling member having means for coupling air and water discharging from the pin member into fluid channels extending to sockets for receiving fluid conduits of the sleeve member to form connections therewith so that fluid is coupled through the coupling member to the cylindrical sleeve member, said coupling member having a recess facing the sleeve member receiving an electrical socket for an electrical element of the illumination means selected from a group consisting of an electrical connection and an electrical lamp, said socket being connected to means for receiving electrical energy from the pin member via slip contact means so that the coupling member may be constructed to alternatively receive a light source for the light-conducting element forming the illumination means of the handpiece and an electrical connection element of an electrical lead to conduct electrical power along the grip sleeve to a light source of the illumination means positioned closer to the head housing whereby both grip sleeves having a light source and grip sleeves having light conducting elements can be used with the handpiece arrangement.

2. In a dental handpiece arrangement according to claim 1, wherein the mounting means for the coupling member mounts the coupling member with a rigid connection to the motor cartridge, and said means for connecting the motor cartridge to the pin member provides a rotational coupling so that the cartridge and coupling member rotate together relative to the pin member.

3. In a dental handpiece according to claim 1, wherein the connection means forms a rigid connection for the motor cartridge with the pin member of the supply line and said mounting means mounts the coupling member for rotation relative to said pin member and said cartridge.

4. In a dental handpiece arrangement according to claim 3, wherein the mounting means includes the motor cartridge containing a tubular heel member of a smaller diameter than the diameter of the bearing surfaces, said coupling member being mounted for rotation on said heel member, and said heel member containing the connection means for the rigid connection to the pin member.

5. In a dental handpiece arrangement according to claim 4, wherein the coupling member contains surfaces coacting with surfaces on the sleeve member to interlock said sleeve member and coupling member to rotate together relative to the motor cartridge.

6. In a dental handpiece arrangement according to claim 4, wherein said sleeve member and coupling member have coacting means to interlock the members together to rotate relative to the motor cartridge.

7. In a dental handpiece arrangement according to claim 6, wherein the sleeve member is part of an adapter having a guide sleeve at one end for being received in a mounting socket of a grip piece, said adapter having a guide channel extending parallel to the axis for receiving a first transmission element for the illumination means, said guide channel at a first end adjacent the coupling member having a size to receive the one end of the first transmission element coacting with the electrical element in the coupling member and at the second end adjacent the guide sleeve having an end of a size to receive the other end of the first transmission element coacting with a second transmission element in the grip piece to provide the light to the work area of the tool.

8. In a dental handpiece arrangement according to claim 7, wherein the first transmission element includes electrical lines, a socket and plug connection at the one end and an electrical element at the other end selects from a group consisting of an electrical lamp and socket, a socket and plug connection and a set of slip ring contact elements.

9. In a dental handpiece arrangement according to claim 8, wherein the first transmission element includes electrical lines received in a rod-shaped tube.

10. In a dental handpiece arrangement according to claim 9, wherein the channel receiving the tubular member is formed by a recess in an inner part of the adapter and is surrounded by an outer sleeve.

11. In a dental handpiece arrangement according to claim 7, wherein the first transmission element is an optical waveguide extending between the first and second ends, said grip piece having an optical waveguide extending from a point adjacent the head housing to a point adjacent the mounting socket, said grip sleeve having means coacting with the adapter to hold the grip sleeve rigidly thereon with the optical waveguide of the grip sleeve aligned with the optical waveguide in the adapter.

12. In a dental handpiece arrangement according to claim 7, wherein the first transmission element is an electrical line having a plug connection positioned in the first end of the channel for forming an electrical connection with the socket in the coupling member and terminating at the second end in a socket for an electric lamp, said grip piece having an optical waveguide extending from a point adjacent the head housing to a point adjacent the mounting socket and said adapter and grip piece having means coacting to hold the optical waveguide of the grip piece in alignment with the lamp at the second end of the channel of the adapter.

13. In a dental handpiece arrangement according to claim 7, wherein the first transmission element comprises an electrical line having a plug connection for forming an electrical connection with the socket of the coupling member and at said second end having means forming an electrical contact, said grip piece having an electrical lamp positioned for projecting light on the work area with electrical leads extending to a point adjacent the mounting socket for forming an electrical contact with the contacts of said transmission element in the adapter.

14. In a dental handpiece arrangement according to claim 13, wherein the electrical contacts are a plug connection.

15. In a dental handpiece arrangement according to claim 13, wherein the electrical contacts in one of said adapter and grip piece comprise slip rings coacting with contacts of the other of the adapter and grip piece.

16. In a dental handpiece arrangement according to claim 6, wherein the sleeve member is part of the grip piece and has a transmission element of the illumination means extending from one end adjacent the coupling member to a point for projecting light at the work surface.

17. In a dental handpiece arrangement according to claim 16, wherein said coupling member has an electrical bulb in said socket and said transmission member being an optical waveguide.

18. In a dental handpiece arrangement according to claim 16, wherein said transmission element comprises an electrical line having means for forming a plug connection with the socket of said coupling member and extending to an electrical lamp adjacent the head housing of the grip piece.

* * * * *